(12) United States Patent
Isch

(10) Patent No.: US 10,376,296 B2
(45) Date of Patent: Aug. 13, 2019

(54) ADJUSTABLE WEDGE IMPLANTS

(71) Applicant: Biomet Manufacturing, LLC, Warsaw, IN (US)

(72) Inventor: Bryce A. Isch, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 252 days.

(21) Appl. No.: 15/617,374

(22) Filed: Jun. 8, 2017

(65) Prior Publication Data

US 2018/0055639 A1     Mar. 1, 2018

Related U.S. Application Data

(60) Provisional application No. 62/378,342, filed on Aug. 23, 2016.

(51) Int. Cl.
*A61F 2/28* (2006.01)
*A61F 2/46* (2006.01)
*A61B 17/80* (2006.01)

(52) U.S. Cl.
CPC ............... *A61B 17/8095* (2013.01)

(58) Field of Classification Search
CPC .................................. A61B 17/8095
See application file for complete search history.

(56) References Cited

U.S. PATENT DOCUMENTS

2003/0195516 A1* 10/2003 Sterett ............... A61B 17/025
606/86 B

* cited by examiner

*Primary Examiner* — Christian A Sevilla
(74) *Attorney, Agent, or Firm* — Schwegman Lundberg & Woessner, P.A.

(57) ABSTRACT

Disclosed is an adjustable wedge for insertion into a bone. The adjustable wedge can include a first arm, a second arm, and an adjustment member. The first arm can have a first end and a second end. The second arm can have a third end and a fourth end. The third end of the second arm can be movably connected to the first end of the first arm. The adjustment member can be in contact with the first arm and the second arm. The adjustment member can be configured to cause an increase or a decrease in a distance between the second end and the fourth end.

21 Claims, 4 Drawing Sheets

ADJUSTABLE WEDGE IMPLANTS

RELATED APPLICATIONS

This application claims the benefit of priority to U.S. Provisional Patent Application Ser. No. 62/378,342, filed Aug. 23, 2016, the content of which is incorporated herein by reference in its entirety.

FIELD OF THE DISCLOSURE

The present disclosure relates to surgical implant systems, including implants, instruments, and methods for installing and extracting an implant. Specifically, the present disclosure relates to adjustable wedge implants.

BACKGROUND

A prosthesis or implant can be positioned in an anatomy, such as a human patient, for various purposes. For example, a prosthesis can be positioned to replace an articulating portion of an anatomy, or correct an anatomic functional deformity. An incorrectly installed or sized implant can result in pain, limit range of motion, increase wear debris, limit stability, and decrease the lifespan of the implant.

SUMMARY

To better illustrate the system disclosed herein, a non-limiting list of examples is provided here:

Example 1 includes an adjustable wedge for insertion into a bone. The adjustable wedge can comprise a first arm, a second arm, and an adjustment member. The first arm having a first end and a second end. The second arm having a third end and a fourth end. The third end of the second arm movably connected to the first end of the first arm. The adjustment member in contact with the first arm and the second arm. The adjustment member configured to cause an increase or a decrease in a distance between the second end and the fourth end.

In Example 2, the adjustable wedge of Example 1 can optionally include the adjustment member including a threaded rod, wherein rotation of the threaded rod in a first direction causes the increase in the distance between the second end and the fourth end and rotation of the threaded rod in a second direction causes the decrease in the distance between the second end and the fourth end.

In Example 3, the adjustable wedge of Example 1 can optionally include the adjustment member includes a jackscrew.

In Example 4, the adjustable wedge of Example 1 can optionally include the adjustment member includes a turnbuckle.

In Example 5, the adjustable wedge of any one of or any combination of Examples 1-4 can optionally include a rib connected to the second end of the first arm and in contact with the fourth end of the second arm.

In Example 6, the adjustable wedge of Example 5 can optionally include the rib including at least one notch configured to allow the rib to fracture to decrease a length of the rib.

In Example 7, the adjustable wedge of Examples 5 can optionally include the rib includes indicia configured to indicate an angle between the first arm and the second arm.

In Example 8, the adjustable wedge of any one of or any combination of Examples 1-7 can optionally include the first arm and the second arm being manufactured from a porous metal.

In Example 9, the adjustable wedge of any one of or any combination of Examples 1-7 can optionally include the first arm and the second arm each including a porous metal coating.

In Example 10, the adjustable wedge of any one of or any combination of Examples 1-9 can optionally include the first arm and the second arm being of differing lengths.

Example 11 can include an apparatus for adjusting a space between bone materials. The apparatus can comprise a connecting member and a plurality of adjustable wedges. Each of the plurality of adjustable wedges can include a first arm, a second arm, and an adjustment member. The first arm having a first end and a second end. The first end movably connected to the connecting member. The second arm having a third end and a fourth end. The third end movably connected to the connecting member. The adjustment member in contact with the first arm and the second arm. The adjustment member configured to cause an increase or a decrease in a distance between the second end and the fourth end.

In Example 12, the apparatus of Example 11 can optionally include the adjustment member including a threaded rod, wherein rotation of the threaded rod in a first direction causes the increase in the distance between the second end and the fourth end and rotation of the threaded rod in a second direction causes the decrease in the distance between the second end and the fourth end.

In Example 13, the apparatus of Example 11 can optionally include the adjustment member including a jackscrew.

In Example 14, the apparatus of Example 11 can optionally include the adjustment member includes a turnbuckle.

In Example 15, the apparatus of any one of or any combination of Examples 11-14 can optionally include each of the adjustable wedges including a rib connected to the second end of the first arm and in contact with the fourth end of the second arm.

In Example 16, the apparatus of Example 15 can optionally include the rib including at least one notch configured to allow the rib to fracture to decrease a length of the rib.

In Example 17, the apparatus of Examples 15 can optionally include the rib including indicia configured to indicate an angle between the first arm and the second arm.

In Example 18, the apparatus of any one of or any combination of Examples 11-17 can optionally include the first arm and the second arm being manufactured from a porous metal.

In Example 19, the apparatus of any one of or any combination of Examples 11-17 can optionally include the first arm and the second arm each including a porous metal coating.

In Example 20, the apparatus of any one of or any combination of Examples 11-19 can optionally include the first arm and the second arm being of differing lengths.

In Example 21, the apparatus of any one of or any combination of Examples 11-20 can optionally include an angle formed by the first arm and the second arm of each of the plurality of wedges being different.

In Example 22, the apparatus of any one of or any combination of Examples 11-21 can optionally include the first arm of each of the plurality of adjustable wedges lying in a common plane.

In Example 23, the apparatus of any one of or any combination of Examples 11-22 can optionally include each of the plurality of adjustable wedges being positionable about the connecting member independently of other adjustable wedges.

Example 24 can include a method of implanting an adjustable wedge into a bone. The method can comprise: creating an osteotomy on a surface of the bone; creating a distraction at a site of the osteotomy, the distraction separating a portion of the bone into a first segment and a second segment separated by a distance; adjusting an angle between a first arm and a second arm of the adjustable wedge; and implanting the adjustable wedge within the distraction.

In Example 25, the method of Example 24 can optionally include increasing the distance separating the first segment and the second segment using the adjustable wedge.

In Example 26, the method of Example 24 can optionally include the adjustable wedge being implanted within the distraction before the angle between the first arm and the second arm of the adjustable wedge is adjusted.

In Example 27, the adjustable wedges or methods of any one of or any combination of Examples 1-26 is optionally configured such that all elements or options recited are available to use or select from.

BRIEF DESCRIPTION OF THE FIGURES

The above-mentioned and other features and advantages of this disclosure, and the manner of attaining them, will become more apparent and the disclosure itself will be better understood by reference to the following description of examples taken in conjunction with the accompanying drawings, wherein.

Corresponding reference characters indicate corresponding parts throughout the several views. The exemplifications set out herein illustrate examples of the disclosure, and such exemplifications are not to be construed as limiting the scope of the disclosure any manner.

DETAILED DESCRIPTION

As used herein, the following directional definitions apply. Anterior and posterior mean nearer the front or nearer the rear of the body, respectively, proximal and distal mean nearer to or further from the root of a structure, respectively, and medial and lateral mean nearer the sagittal plane or further from the sagittal plane, respectively. The sagittal plane is an imaginary vertical plane through the middle of the body that divides the body into right and left halves. In addition, the terms implant and prosthesis, and variations thereof, can be used interchangeably.

Patients can suffer from various inflictions that can cause a need for a wedge to be implanted into bone or between bones. For example, a patient can suffer from trauma to a limb, a birth defect, etc. that can cause a need for surgical reconstruction or manipulation of a bone.

Traditionally, wedges are offered having a variety of fixed angles and a surgeon is required to select a wedge that closely matches a desired angle. The selection of stock angle wedges, or fixed angle wedges, does not allow the surgeon to customize an implant. For instance, using fixed angle wedges, the angle of a distraction can only be set to fixed angles.

As disclosed herein, an adjustable wedge, or a collection of adjustable wedges can be used to allow a surgeon to customize an implant. The use of adjustable wedges can also decrease costs because surgical kits need not be manufactured with a plurality of fixed angled wedges. Instead, an adjustable angle wedge can replace the plurality of fixed angle wedges thereby decreasing costs and allowing for a more customized implant.

Figure 1:
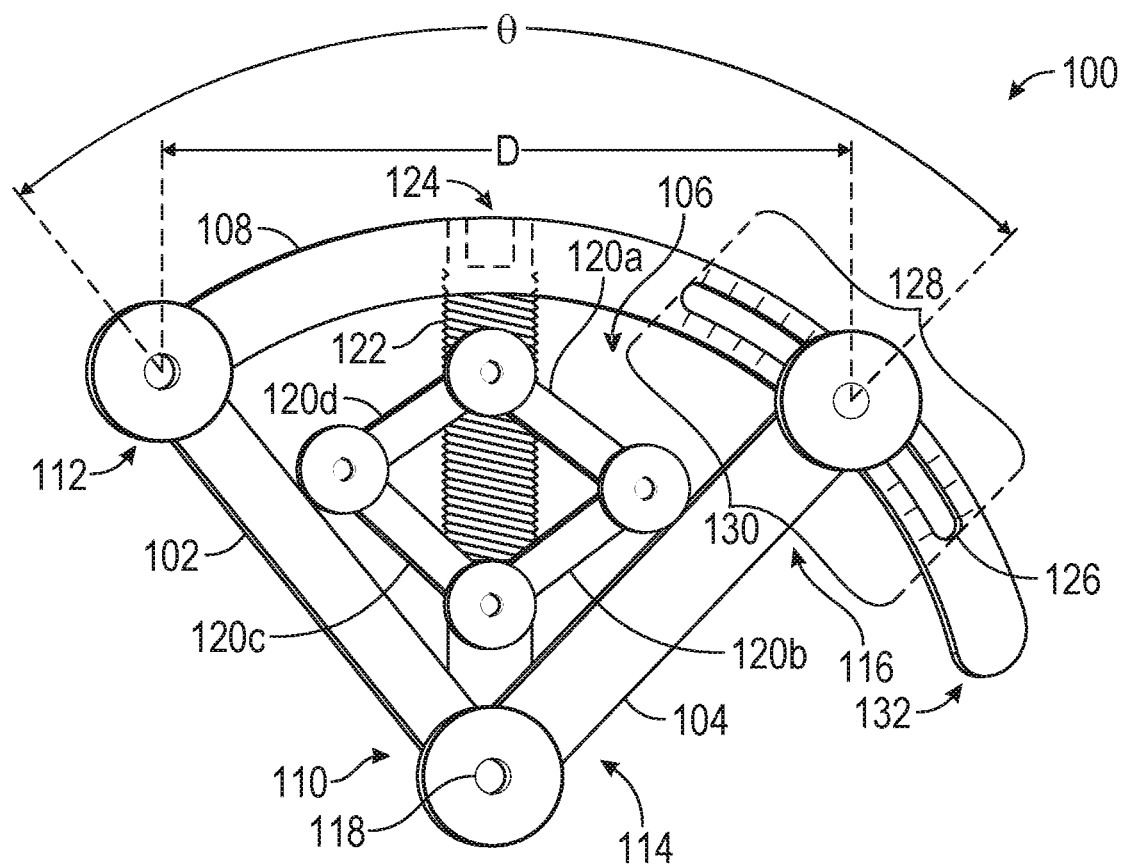
FIG. 1 shows an example of an adjustable wedge in accordance with at least one example of the present disclosure.

Turning now to the figures, FIG. 1 shows an adjustable wedge 100 in accordance with at least one example disclosed herein. The adjustable wedge 100 can include a first arm 102, a second arm 104, an adjustment member 106, and a rib 108. As shown in FIG. 1, the first arm 102 can include a first end 110 and a second end 112. The second arm 104 can include a third end 114 and a fourth end 116. The first end 110 can be movably connected to the third end 114. For example, a pin 118 can pass through the first arm 102 and the second arm 104 at the first end 110 and the third end 114, respectively. The pin 118 can allow the first arm 102 and the second arm 104 to pivot relative to one another. Stated another way, the first arm 102 and the second arm 104 can be pivotably connected to one another. In addition, the first arm 102 and the second arm 104 can be different lengths. The first arm 102 and the second arm 104 can also be the same length.

The angle θ formed by the first arm 102 and the second arm 104 can vary. For example, as described herein, the adjustment member 106 can be used to increase or decrease a distance D between the second end 112 and the fourth end 116. In other words, changes in the distance D can correspond to changes in the angle θ and vice versa.

As shown in FIG. 1, the adjustment member 106 can include a jackscrew. As such, the adjustment member 106 can include a plurality of links 120a, 120b, 120c, and 120d (collectively links 120) and a threaded rod 122. The threaded rod 122 can be secured to the first arm 102 and the second arm 104 proximate the first end 110 and the third end 114. The threaded rod 122 can include a head 124 that can engage a tool (not shown). The tool can be used to rotate the threaded rod 122. For example, the head 124 can be a hex-head, slotted head, or Phillips-head and a socket, Allen wrench, or screwdriver can be used to rotate the threaded rod 122.

Rotation of the threaded rod 122 in a first direction (e.g., clockwise) can cause the portions of the links 120a and 120d connected to the threaded rod 122 to translate in a direction toward the portions of the links 120b and 120c connected to the threaded rod 122. The translation can cause the portions of the links 120 not connected to the threaded rod 122 to translate in a direction away from the threaded rod 122. The translation can cause the links 120 to apply a force to the first arm 102 and the second arm 104. The force can cause movement of the first arm 102 and the second arm 104 such that the angle θ and distance D increase.

Rotation of the threaded rod 122 in a second direction (e.g., counter-clockwise) can cause the portions of the links 120a and 120d connected to the threaded rod 122 to translate in a direction away from the portions of the links 120b and 120c connected to the threaded rod 122. The translation can cause the portions of the links 120 not connected to the threaded rod 122 to translate in a direction towards the threaded rod 122. The translation can cause the links 120 to permit the first arm 102 and the second arm 104 to be moved such that the angle θ and distance D decrease.

The links 120 can be connected to the first arm 102 and the second arm 104 in some examples. Other examples can include the links 120 not being connected to the first arm 102 and the second arm 104. For example, when the links 120 are not connected to the first arm 102 and the second arm 104, rotation of the threaded rod 122 in the second direction can cause the links 120 to break contact with the first arm 102 and the second arm 104. A surgeon can then position the first arm 102 and the second arm 104 to achieve a desired angle. Once the desired angle in achieved, the surgeon can rotate the threaded rod 122 in the first direction to set the angle θ and distance D.

The rib 108 can connect the second end 112 and the fourth end 116. The rib 108 can have a constant radius of curvature. For example, if the first arm 102 and the second arm 104 are of the same length, the radius of curvature of the rib 108 can be the length of the first arm 102 and the second arm 104. When the radius of curvature of the rib 108 is constant, the rib 108 can be connected to the first arm 102 in a fixed position. When the radius of curvature of the rib 108 is not constant, the rib 108 can be connected to the first arm 102 in a pivoting manner. In other words, when the radius of curvature of the rib 108 is not constant, the rib 108 can rotate about a point proximate the second end 112.

During movement of the second arm 104 relative to the first arm 102, the fourth end 116 can translate within a slot 126. The slot 126 can include indicia 128. The indicia 128 can indicate a measure of the angle θ. For example, the indicia 128 can include markings graduated in 5° increments.

The rib 108 can also include scores or notches 130 that can facilitate fracture of the rib 108 in order to shorten the rib 108. For example, once the angle θ is set, a portion 132 of the rib 208 can be removed. The notches 130 and the indicia 128 can coincide with one another. For example, the notches 130 can be the indicia 128.

Figure 2:
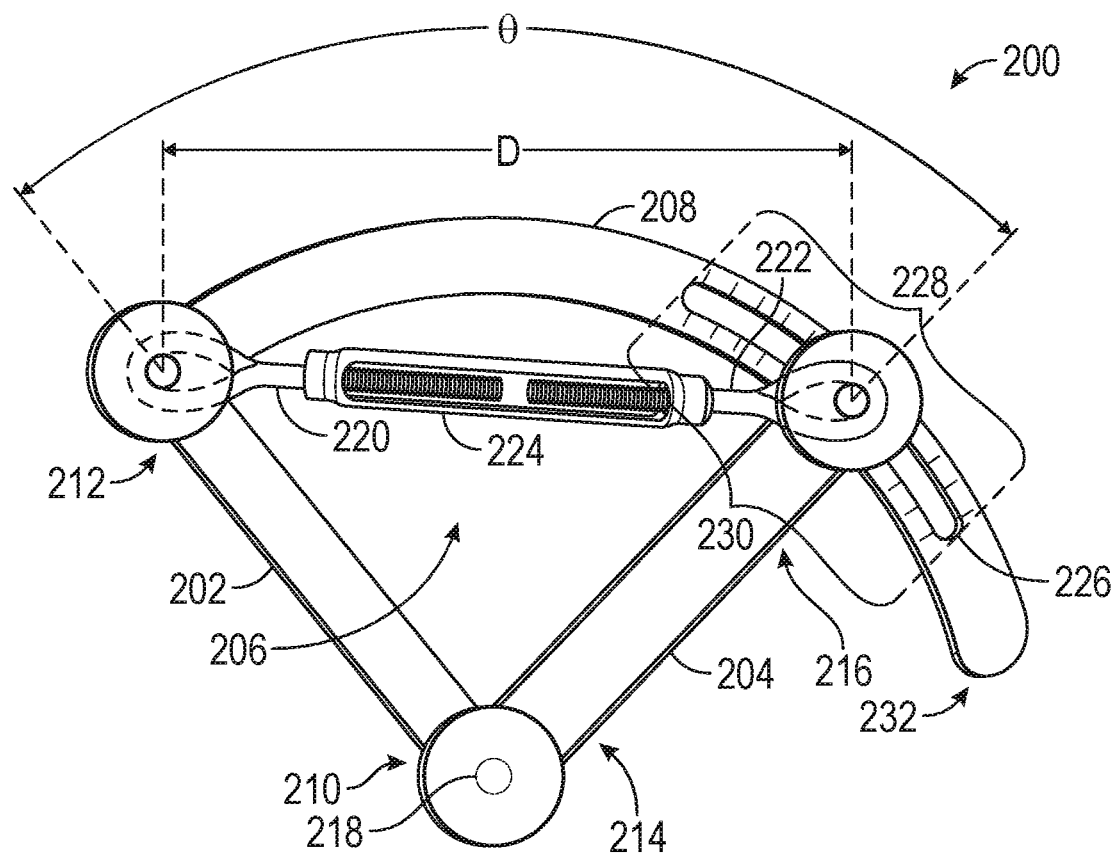
FIG. 2 shows an example of an adjustable wedge in accordance with at least one example of the present disclosure.

FIG. 2 shows an adjustable wedge 200 in accordance with at least one example disclosed herein. The adjustable wedge 200 can include a first arm 202, a second arm 204, an adjustment member 206, and a rib 208. As shown in FIG. 2, the first arm 202 can include a first end 210 and a second end 212. The second arm 204 can include a third end 214 and a fourth end 216. The first end 210 can be movably connected to the third end 214. For example, a pin 218 can pass through the first arm 202 and the second arm 204 at the first end 210 and the third end 214, respectively. The pin 218 can allow the first arm 202 and the second arm 204 to pivot relative to one another. Stated another way, the first arm 202 and the second arm 204 can be pivotably connected to one another. In addition, the first arm 202 and the second arm 204 can be different lengths. The first arm 202 and the second arm 204 can also be the same length.

The angle θ formed by the first arm 202 and the second arm 204 can vary. For example, as described herein, the adjustment member 206 can be used to increase or decrease a distance D between the second end 212 and the fourth end 216. In other words, changes in the distance D can correspond to changes in the angle θ and vice versa.

As shown in FIG. 2, the adjustment member 206 can include a turnbuckle. As such, the adjustment member 206 can include a first threaded rod 220, a second threaded rod 222, and a nut 224. The first threaded rod 220 can be secured to the first arm 202 and the second threaded rod 222 can be secured to the second arm 204. The nut 224 can include a shape that can engage a tool (not shown). The tool can be used to rotate the nut 224. For example, the nut 224 can be a hexagonal shape and a wrench can be used to rotate the nut 224.

Rotation of the nut 224 in a first direction (e.g., clockwise) can cause the first threaded rod 220 and the second threaded rod 222 to translate in a direction away from the nut 224. The translation can cause the first threaded rod 220 and the second threaded rod 222 to apply a force to the first arm 202 and the second arm 204. The force can cause movement of the first arm 202 and the second arm 204 such that the angle θ and distance D increase.

Rotation of the nut 224 in a second direction (e.g., counter-clockwise) can cause the first threaded rod 220 and the second threaded rod 222 to translate in a direction towards the nut 224. The translation can cause the first threaded rod 220 and the second threaded rod 222 to apply a force to the first arm 202 and the second arm 204. The force can cause movement of the first arm 202 and the second arm 204 such that the angle θ and distance D decrease. During surgery, a surgeon can rotate the nut 224 to position the first arm 202 and the second arm 204 to achieve a desired angle.

The rib 208 can connect the second end 212 and the fourth end 216. The rib 208 can have a constant radius of curvature. For example, if the first arm 202 and the second arm 204 are of the same length, the radius of curvature of the rib 208 can be the length of the first arm 202 and the second arm 204. When the radius of curvature of the rib 208 is constant, the rib 208 can be connected to the first arm 202 in a fixed position. When the radius of curvature of the rib 208 is not constant, the rib 208 can be connected to the first arm 202 in a pivoting manner. In other words, when the radius of curvature of the rib 208 is not constant, the rib 208 can rotate about a point proximate the second end 212.

During movement of the second arm 204 relative to the first arm 202, the fourth end 216 can translate within a slot 226. The slot 226 can include indicia 228. The indicia 228 can indicate a measure of the angle θ. For example, the indicia 228 can include markings graduated in 5° increments.

The rib 208 can also include scores or notches 230 that can facilitate fracture of the rib 208 in order to shorten the rib 208. For example, once the angle θ is set, a portion 232 of the rib 208 can be removed. The notches 230 and the indicia 228 can coincide with one another. For example, the notches 230 can be the indicia 228.

Figure 3:
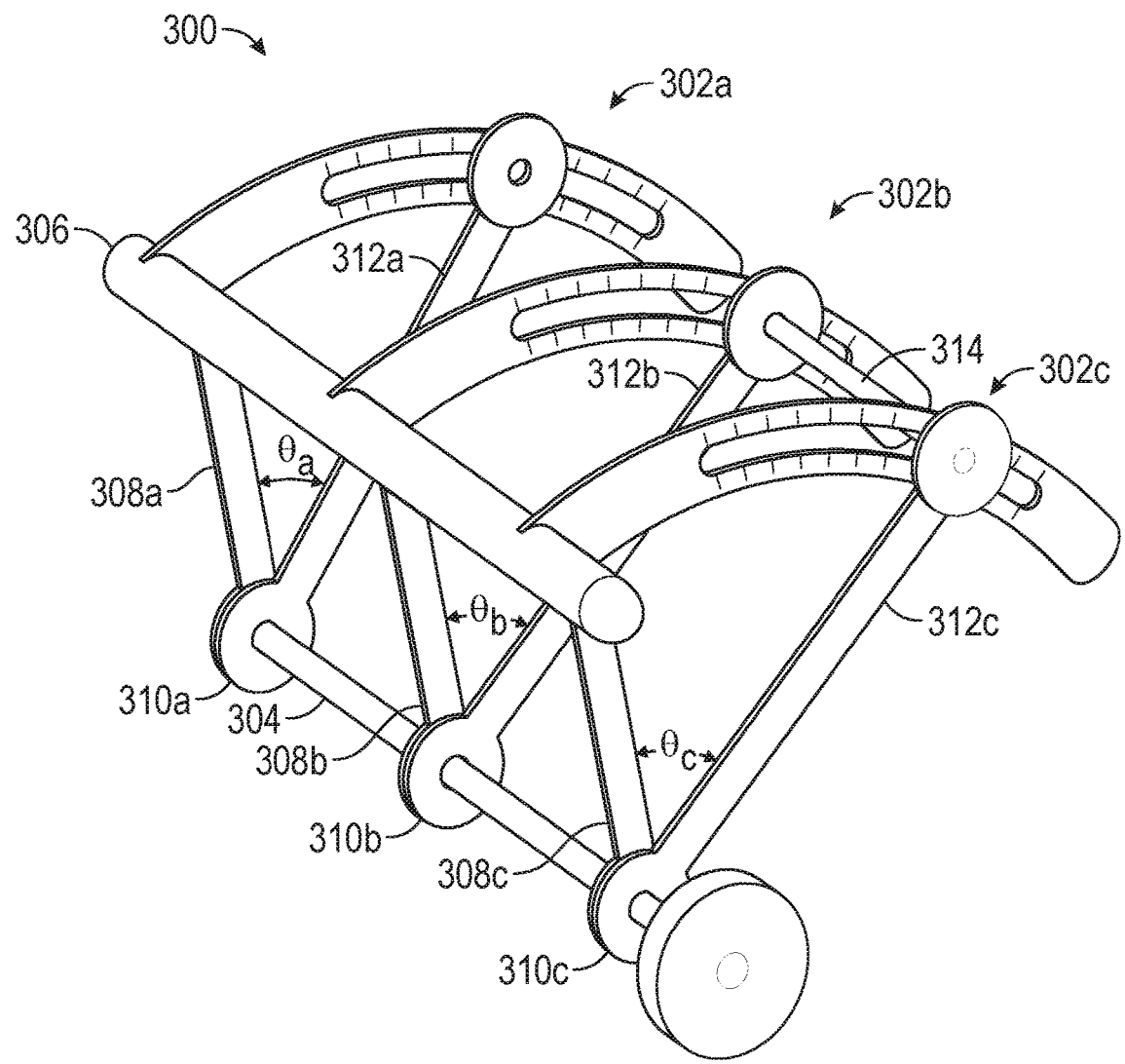
FIG. 3 shows an example of an apparatus including multiple adjustable wedges in accordance with at least one example of the present disclosure.

FIG. 3 shows an example of an apparatus 300 including multiple adjustable wedges 302a, 302b, and 302c (collectively adjustable wedges 302) in accordance with at least one example of the present disclosure. The adjustable wedges 302 can be structured similar to the adjustable wedge 100, the adjustable wedge 200, or a combination of both. The adjustable wedges 302 can be connected by a first connecting member 304. For example, the first connecting member 304 can pass through a portion of the adjustable wedges 302 and act as a pivot point for each of the adjustable wedges. A second connecting member 306 also can be used to connect the adjustable wedges 302 to one another. While FIG. 3 shows three adjustable wedges 302, any number of adjustable wedges 302 can be included in the apparatus 300. Furthermore, while FIG. 3 shows each of the adjustable wedges 302 connected via the second connecting member 306, the second connecting member 306 can connect a subset of the adjustable wedges 302. For instance, the second connecting member 306 can connect adjustable wedges 302a and 302b or adjustable wedges 302b and 302c.

As shown in FIG. 3, the second connecting member 306 can connect first arms 308a, 308b, and 308c (collectively first arms 308) of each of the adjustable wedges 302 together. Connecting the first arms 308 together can cause the first arms to lie in a common plane. In addition, the second connecting member 306 can add structural rigidity to the apparatus 300.

Each of the adjustable wedges 302 can be pivotable about the first connecting member 304. For example, the adjustable wedge 302a can be rotated about the first connecting member 304 independently of the adjustable wedges 302b and 302c. Once each of the adjustable wedges 302 is in a desired orientation relative to one another, set screws 310a, 310b, and 310c (collectively set screws 310) or other locking member can be used to fix each of the adjustable wedges 302 in the desired orientation.

Furthermore, when the second connecting member 306 does not connect all of the adjustable wedges 302, any non-connected adjustable wedges can rotate about the first connecting member 304 independent of other adjustable wedges. For example, if the second connecting member 306 connects adjustable wedges 302a and 302b, then adjustable wedge 302c can rotation about the first connecting member 304 independent of the adjustable wedges 302a and 302b.

Second arms 312a, 312b, and 312c (collectively 312) can be connected. For example, as shown in FIG. 3, second arms 312b and 312c can be connected to a third connecting member 314, while second arm 312a is free to move independently of the second arms 312h and 312c. The third connecting member 314 can allow angles θa, θb, and θc (collectively angles θ) to be adjusted simultaneously. The adjustment mechanism for the adjustable wedges 302 has been omitted from FIG. 3 for clarity purposes. However, one or more of the adjustable wedges 302 can have an adjustment member as described herein. The adjustment member or adjustment members can be used to adjust one or more of the angles θ. For instance, an adjustment member operably connected to the adjustable wedge 302b can adjust angles θb and θc simultaneously and an adjustment member operably connected to the adjustable wedge 302a can adjust angle θa independently of angles θb and θc.

The adjustable wedge shown in FIGS. 1-3 can be manufactured from metals, polymers, ceramics, or any combination thereof. For example, the adjustable wedges can be manufactured from a polymer and coated with a porous metal. In addition, the adjustable wedges can be manufactured using various manufacturing processes. For example, the adjustable wedges can be machined from billet materials, injection molded, 3D printed, cast, etc. Furthermore, multiple manufacturing techniques can be used to manufacture the adjustable wedges. For example, the various components can be machined from surgical grade stainless steel or cobalt and the indicia or scores can be laser etched onto the ribs.

Figure 4:
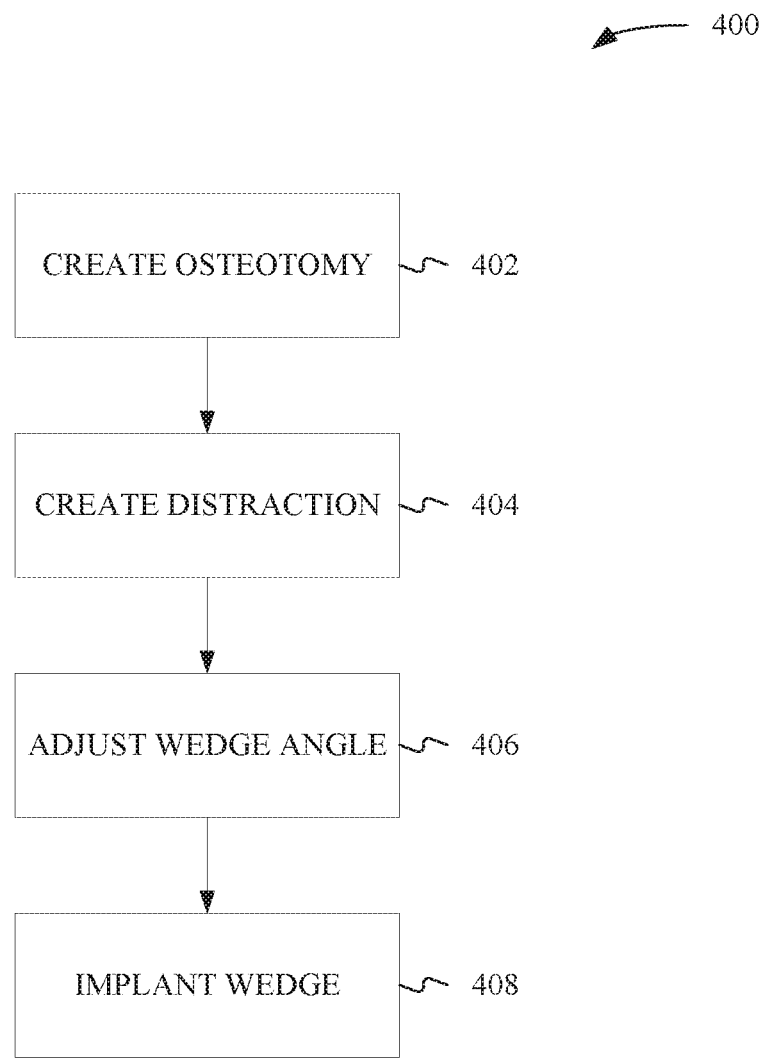
FIG. 4 shows an example method for installing an adjustable wedge in accordance with at least one example of the present disclosure.

FIG. 4 shows a flowchart for a method 400 of implanting one or more adjustable wedges in accordance with at least one example disclosed herein. For example, using the method 400, the adjustable wedge 100, the adjustable wedge 200, or the apparatus 300 can be implanted within a patient. The method 400 can begin at stage 402 where an osteotomy can be created. For example, a patient can have a foot injury or other disorder warranting the need to have an adjustable wedge implanted in his or her foot. As such, at stage 402, an osteotomy can be created on the surface of a medial cuneiform or calcaneocuboid joint.

From stage 402, the method 400 can proceed to stage 404 where a distraction can be created. For example, the distraction can be created at the site of the osteotomy. The distraction can be used to create space for the adjustable wedge. The extent of the distraction can depend on the injury or other disorder that is the genesis of the need for the implantation of the adjustable wedge.

From stage 404, the method can proceed to stage 406 where an angle of the adjustable wedge can be adjusted. For example, as described above, the angle or angles θ can be adjusted to a desired position such that the adjustable wedge fits properly within the distraction. Once the angle of the adjustable wedge has been set, the method can proceed to stage 408 where the adjustable wedge can be installed within the distraction.

The adjustable wedge can also be used to assist in creating the distraction. For example, the adjustable wedge can be implanted, partially or completely, within the distraction and the angle adjusted to create the final size of the distraction. For instance, the initial distraction can cause a deflection in the cuneiform of X degrees, After the adjustable wedge is implanted, the angle θ can be adjusted to increase the deflection in the cuneiform to Y degrees. In other words, the adjustable wedge can be installed within the distraction before the angle between a first arm and a second arm of the adjustable wedge is set. After the adjustable wedge is installed, the angle between the first arm and the second arm of the adjustable wedge can be set to finalize a size of the distraction. In addition, once the adjustable wedge is implanted, a plate or other structure can be secured to the bone (i.e., the cuneiform or the calcaneocuboid) to secure the adjustable wedge in place.

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims.

What is claimed is:

1. An adjustable wedge for insertion into a bone, the adjustable wedge comprising:
   a first arm having a first end and a second end;
   a second arm having a third end and a fourth end, the third end of the second arm movably connected to the first end of the first arm;
   an adjustment member in contact with the first arm and the second arm, the adjustment member configured to cause an increase or a decrease in a distance between the second end and the fourth end; and
   a rib connected to the second end of the first arm and in contact with the fourth end of the second arm.

2. The adjustable wedge of claim 1, wherein the adjustment member includes a threaded rod, wherein rotation of the threaded rod in a first direction causes the increase in the distance between the second end and the fourth end and rotation of the threaded rod in a second direction causes the decrease in the distance between the second end and the fourth end.

3. The adjustable wedge of claim 1, wherein the adjustment member includes a jackscrew.

4. The adjustable wedge of claim 1, wherein the adjustment member includes a turnbuckle.

5. The adjustable wedge of claim 1, wherein the rib includes at least one notch configured to allow the rib to fracture to decrease a length of the rib.

6. The adjustable wedge of claim 1, wherein the rib includes indicia configured to indicate an angle between the first arm and the second arm.

7. The adjustable wedge of claim 1, wherein the first arm and the second arm are manufactured from a porous metal.

8. The adjustable wedge of claim 1, wherein the first arm and the second arm each includes a porous metal coating.

9. The adjustable wedge of claim 1, wherein the first arm and the second arm are of differing lengths.

10. An apparatus for adjusting a space between bone materials, the apparatus comprising:
    a connecting member; and
    a plurality of adjustable wedges, each of the plurality of adjustable wedges including:
        a first arm having a first end and a second end, the first end movably connected to the connecting member;
        a second arm having a third end and a fourth end, the third end movably connected to the connecting member; and
        an adjustment member in contact with the first arm and the second arm, the adjustment member configured to cause an increase or a decrease in a distance between the second end and the fourth end.

11. The apparatus of claim 10, wherein the adjustment member includes a threaded rod, wherein rotation of the threaded rod in a first direction causes the increase in the distance between the second end and the fourth end and rotation of the threaded rod in a second direction causes the decrease in the distance between the second end and the fourth end.

12. The apparatus of claim 10, wherein the adjustment member includes a jackscrew.

13. The apparatus of claim 10, wherein each of the adjustable wedges includes a rib connected to the second end of the first arm and in contact with the fourth end of the second arm.

14. The apparatus of claim 10, wherein the first arm and the second arm are of differing lengths.

15. The apparatus of claim 10, wherein an angle formed by the first arm and the second arm of each of the plurality of wedges is different.

16. The apparatus of claim 10, wherein the first arm of each of the plurality of adjustable wedges lie in a common plane.

17. The apparatus of claim 10, wherein each of the plurality of adjustable wedges is positionable about the connecting member independently of other adjustable wedges.

18. A method of implanting an adjustable wedge into a bone, the method comprising:
    creating an osteotomy on a surface of the bone;
    creating a distraction at a site of the osteotomy, the distraction separating a portion of the bone into a first segment and a second segment separated by a distance;
    adjusting an angle between a first arm and a second arm of the adjustable wedge; and
    implanting the adjustable wedge within the distraction.

19. The method of claim 18, further comprising increasing the distance separating the first segment and the second segment using the adjustable wedge, and wherein the adjustable wedge is implanted within the distraction before the angle between the first arm and the second arm of the adjustable wedge is adjusted.

20. An adjustable wedge for insertion into a bone, the adjustable wedge comprising:
    a first arm having a first end and a second end;
    a second arm having a third end and a fourth end, the third end of the second arm movably connected to the first end of the first arm; and
    an adjustment member in contact with the first arm and the second arm, the adjustment member configured to cause an increase or a decrease in a distance between the second end and the fourth end,
    wherein the first arm and the second arm are manufactured from a porous metal.

21. An adjustable wedge for insertion into a bone, the adjustable wedge comprising:
    a first arm having a first end and a second end;
    a second arm having a third end and a fourth end, the third end of the second arm movably connected to the first end of the first arm; and
    an adjustment member in contact with the first arm and the second arm, the adjustment member configured to cause an increase or a decrease in a distance between the second end and the fourth end,
    wherein the first arm and the second arm each includes a porous metal coating.

\* \* \* \* \*